(12) United States Patent
Ratner

(10) Patent No.: US 10,258,759 B2
(45) Date of Patent: *Apr. 16, 2019

(54) BI-LEVEL POSITIVE AIRWAY PRESSURE DEVICE

(71) Applicant: MERCURY ENTERPRISES, INC., Clearwater, FL (US)

(72) Inventor: Jeffrey B. Ratner, Pinellas Park, FL (US)

(73) Assignee: MERCURY ENTERPRISES, INC., Clearwater, FL (US)

(*) Notice: Subject to any disclaimer, the term of this patent is extended or adjusted under 35 U.S.C. 154(b) by 825 days.

This patent is subject to a terminal disclaimer.

(21) Appl. No.: 14/853,079

(22) Filed: Sep. 14, 2015

(65) Prior Publication Data

US 2016/0074607 A1   Mar. 17, 2016

Related U.S. Application Data

(60) Provisional application No. 62/050,554, filed on Sep. 15, 2014.

(51) Int. Cl.
*A61M 16/00*    (2006.01)
*A61M 16/20*    (2006.01)

(52) U.S. Cl.
CPC ........ *A61M 16/208* (2013.01); *A61M 16/207* (2014.02); *A61M 2016/003* (2013.01); *A61M 2016/0027* (2013.01); *A61M 2205/3331* (2013.01)

(58) Field of Classification Search
CPC .............. A61M 16/208; A61M 16/207; A61M 2016/003; A61M 2016/0027; A61M 2205/3331
See application file for complete search history.

(56) References Cited

U.S. PATENT DOCUMENTS

| 5,002,050 | A | * | 3/1991 | McGinnis | ........... A61M 16/208 |
| | | | | | 128/204.18 |
| 5,438,980 | A | * | 8/1995 | Phillips | ................. A61M 16/20 |
| | | | | | 128/204.21 |
| 5,896,857 | A | * | 4/1999 | Hely | ........................ A62B 9/02 |
| | | | | | 128/203.11 |
| 6,253,764 | B1 | * | 7/2001 | Calluaud | ............... A61M 16/20 |
| | | | | | 128/204.18 |

(Continued)

*Primary Examiner* — Steven O Douglas
(74) *Attorney, Agent, or Firm* — Larson & Larson, P.A.; Frank Liebenow; Justin P. Miller

(57) ABSTRACT

A bi-level positive airway pressure device includes a housing that has a patient port for connecting to an airway of a patient. Within the housing is a device that generates a positive airway pressure directed towards to patient port. Also within the housing is a system that mechanically detects exhalation (by the patient that is connected to the patient port) that enters into the patient port. Responsive to detecting exhalation, a blocking device occludes the device that generates positive airway pressure, thereby reducing or stopping the positive airway pressure until the system that mechanically detects exhalation no longer detects exhalation, at which time the blocking device is operated to no longer occlude the device for generating positive airway pressure, thereby providing positive airway pressure to the patient port during, for example, inhalation.

18 Claims, 5 Drawing Sheets

(56) References Cited

U.S. PATENT DOCUMENTS

| | | | |
|---|---|---|---|
| 2008/0078395 A1* | 4/2008 | Ho ..................... | A61M 16/208 128/205.24 |
| 2014/0150793 A1 | 6/2014 | Douglas et al. | |
| 2016/0074607 A1* | 3/2016 | Ratner ................ | A61M 16/208 128/204.23 |
| 2017/0232224 A1* | 8/2017 | Ratner ................ | A61M 16/208 128/204.25 |
| 2018/0021532 A1* | 1/2018 | Ratner ................ | A61M 16/208 128/204.26 |

* cited by examiner

BI-LEVEL POSITIVE AIRWAY PRESSURE DEVICE

CROSS-REFERENCE TO RELATED APPLICATION

This application claims the benefit of U.S. provisional application No. 62/050,554 filed on Sep. 15, 2014, the disclosure of which is incorporated by reference.

FIELD

This invention relates to the field of medicine and more particularly to an apparatus for delivering bi-level positive airway pressure.

BACKGROUND

Patients (e.g. mammals such as humans) having respiratory issues such as chronic obstructive pulmonary disease (COPD), sleep apnea, etc., often require assistance in filling their lungs with air, or inhalation. There exist devices that are interfaced to a patient's airway for providing such assistance by injecting a positive airway pressure towards and into the patient' airway, thereby assisting that patient with inhalation.

One type of device for providing such assistance is a Continuous Positive Airway Pressure (CPAP) device as described in, for example, U.S. Pat. No. 4,944,310. Continuous Positive Airway Pressure devices generally provide a gas pressure that is slightly greater than ambient air pressure into the patient's airway. Continuous Positive Airway Pressure devices work well for certain patients, but patients that have poor lung capability often find it harder to exhale due to the constant added pressure directed into their air passages by the Continuous Positive Airway Pressure device, being that the Continuous Positive Airway Pressure device continues to provide positive air pressure, even while the patient is exhaling.

Bi-level Positive Airway Pressure devices address this issue of exhalation as described above by detecting when the patient is exhaling and reducing the positive airway pressure until the patient completes exhalation and starts inhalation. In such, there are two different positive airway pressures delivered (hence bi-level), a higher positive airway pressure while the patient inhales and a lower positive airway pressure (e.g., atmospheric pressure) while the patient exhales.

To accomplish the bi-level positive airway pressure delivery, Bi-level Positive Airway Pressure devices of current have electrical transducers that senses when the patient is exhaling and an electrical circuit that receives an electrical signal from the transducers and responsive to that signal, modulates the positive airway pressure between two values. For example, U.S. Pat. Pub. 20140150793 describes such a Bi-level Positive Airway Pressure device that has a flow sensor connected to a controller. This device has a blower for providing the positive airway pressure. Upon detecting that a patient is exhaling, the controller sets the blower to operate at a lower speed (or off), thereby reducing the positive airway pressure until the patient stops exhaling, at which time the controller detects the end of the exhalation and restarts the blower.

The above described Bi-level Positive Airway Pressure devices are known to function well, especially with patients that have very little lung capacity. Unfortunately, many such patients are not limited to bed rest and wish to be mobile. It is known to provide the pressure component for positive airway pressure by a portable device, typically portable Continuous Positive Airway Pressure (CPAP) devices. Such devices typically derive the pressure component for positive airway pressure from a small battery operated pump or through a compressed gas cylinder (e.g. air, oxygen, etc.). It is possible, especially if made small and light enough to be carried by the patient. The sensors, the connections to the sensors, and the added electronics make portability hard to accomplish, especially if a compressed gas tank us utilized. Further, the issues related to battery charge maintenance become an issue.

What is needed is a bi-level positive airway pressure system that has an entirely mechanical system for switching between pressures.

SUMMARY

In one embodiment, a bi-level positive airway pressure device is disclosed including a housing that has a patient port for connecting to an airway of a patient. Within the housing is a device such as a nozzle that generates a positive airway pressure directed towards to patient port. Also within the housing is a system that mechanically detects exhalation (by the patient connected to the patient port) entering into the patient port. Responsive to detecting exhalation, a blocking device occludes the device that generating positive airway pressure, thereby reducing or stopping the positive airway pressure until the system that mechanically detects exhalation no longer detects exhalation, at which time the blocking device is operated to no longer occlude the device for generating positive airway pressure, thereby providing positive airway pressure to the patient port during, for example, inhalation.

In another embodiment, a bi-level positive airway pressure device is disclosed including a housing having a patient port for connecting to an airway of a patient. The bi-level positive airway pressure device has mechanisms for generating a positive airway pressure directed towards the patient port and mechanisms for detecting exhalation entering into the patient port. Mechanisms are provided for selectively blocking the positive airway pressure, blocking the positive airway pressure when the mechanism for detecting exhalation detects exhalation (e.g. the patient breaths out), thereby making it easier for the patient to exhale.

In another embodiment, a bi-level positive airway pressure device is disclosed including a housing having a patient port for connecting to an airway of a patient. A nozzle generates a positive airway pressure directed towards the patient port. The nozzle is positioned near an end of the housing distal from the patient port. A mechanical device for detecting an exhalation flow entering into the patient port is coupled to a occluding member such that upon detection of the exhalation flow, the mechanical device causes the occluding member to block the nozzle, thereby abating the positive airway pressure.

In another embodiment, a bi-level positive airway pressure device is disclosed including a housing having a patient port at one end for interfacing to an airway of a patient. A nozzle that is interfaced to a supply of gas generates a positive airway pressure in a direction aimed at the patient port. The nozzle situated at an end of the housing distal from the patient port and the nozzle is directed towards the patient port. An occluding member is movably positioned between the nozzle and the patient port and is positionable in at least two positions. A first position blocks the positive airway pressure and a second position allows flow of the positive airway pressure to the patient port. A gas jet is initially aimed at a first port and during exhalation; the gas jet deflects to be aimed at a second port. The first port is in fluid communications with a first mechanical device that moves the occluding member to the second position when the first mechanical device (e.g., diaphragm) receives pressure from the gas jet, thereby enabling the positive airway pressure. The second port is in fluid communications with a second mechanical device that moves the occluding member to the first position when the second mechanical device (e.g., diaphragm) receives pressure from the gas jet, thereby abating the positive airway pressure when the exhalation flow is detected.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1A:
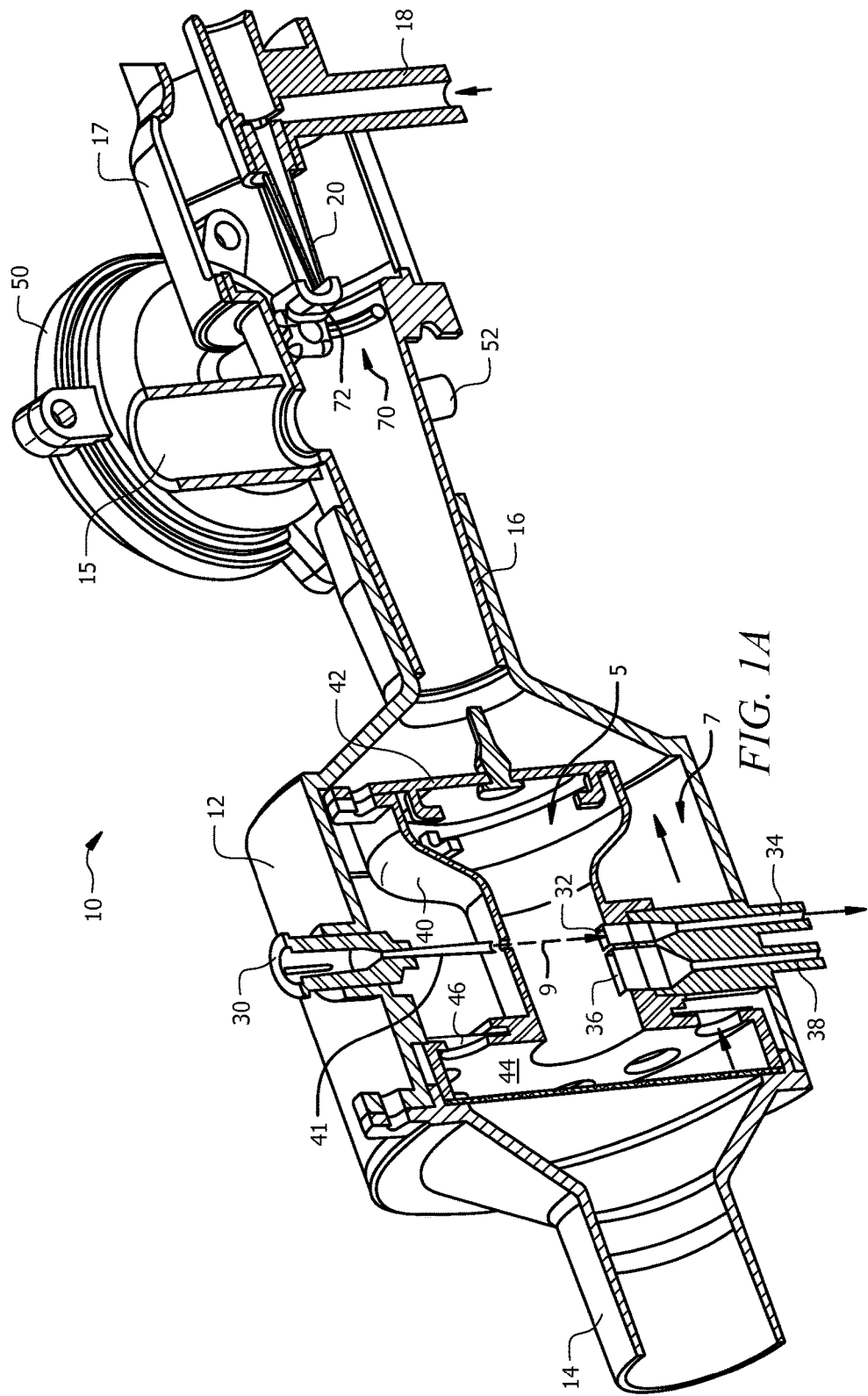
FIGS. 1A and 1B illustrate cut-away views of a mechanical bi-level positive airway pressure system.

Reference will now be made in detail to the presently preferred embodiments of the invention, examples of which are illustrated in the accompanying drawings. Throughout the following detailed description, the same reference numerals refer to the same elements in all figures.

Figure 1B:
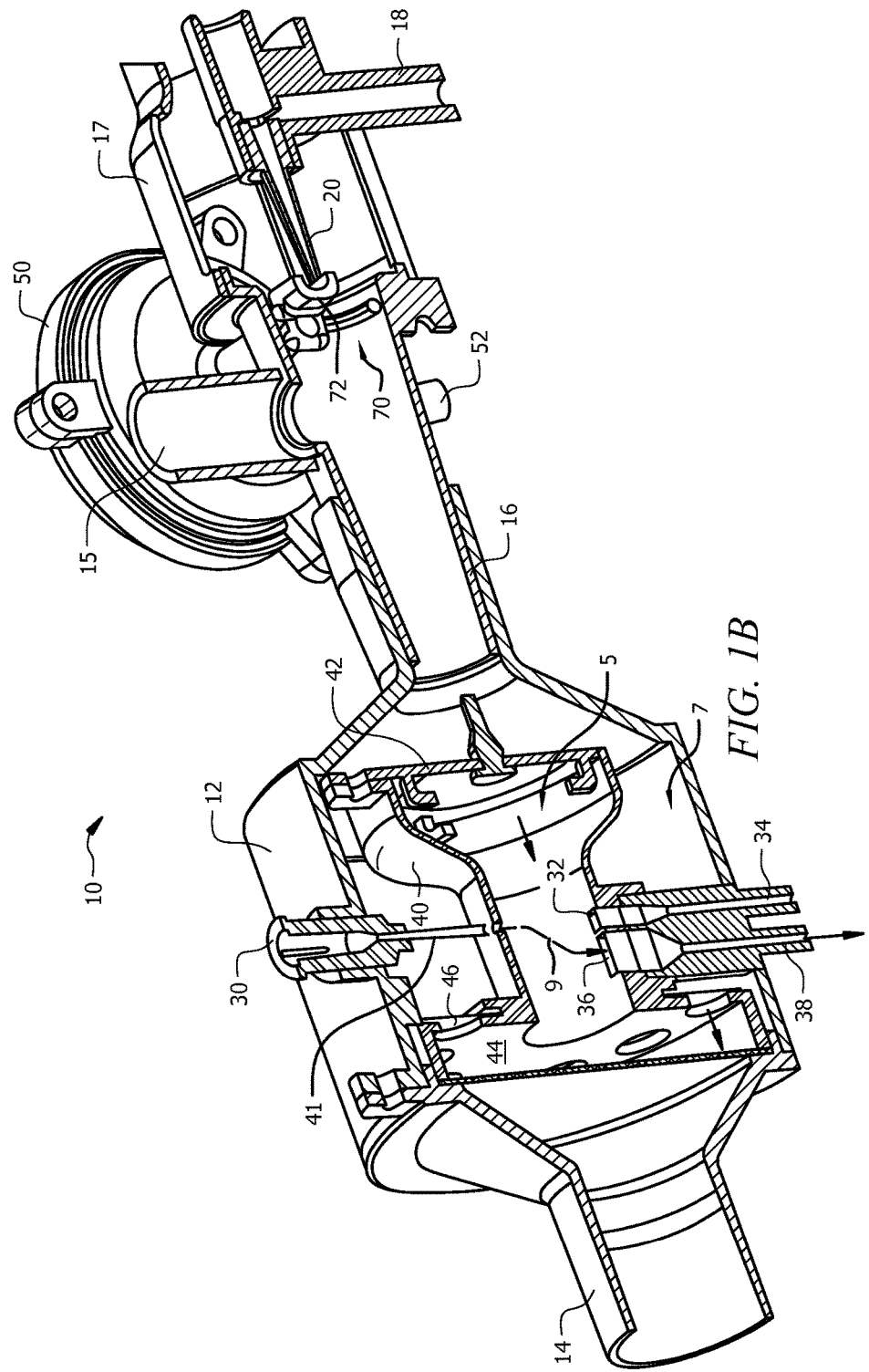

Referring to FIGS. 1A and 1B, cut-away views of a mechanical bi-level positive airway pressure system 10 are shown. The principles of operation of the bi-level positive airway pressure system 10 are understandable from FIGS. 1A and 1B.

In FIGS. 1A and 1B, the patient airway (not shown) is interfaced to the patient port 14 by any way known in the industry such as by a nasal cannula, face mask, etc.

As shown in FIG. 1A, during exhalation, the flow of air from the patient travels through the outer chamber 7 of the detection section 12 as indicated by the air flow arrow. A first one-way valve 44/46 allows flow in the exhalation direction through the outer chamber (indicated by an arrow) while a second one-way valve 40/42 precludes flow through the inner chamber 5 defined by an inner structure 40.

As shown in FIG. 1B, during inhalation, the one-way valves 44/46/40/42 operate in an opposing fashion, in that, the flow of air from the positive pressure nozzle 20 (optionally along with atmospheric air) travels through the inner chamber 5 of the detection section 12 as indicated by the inhalation air flow arrow in FIG. 1B. The first one way valve 44/46 blocks flow in the inhalation so there is no flow through the outer chamber 7 while the second one-way valve 40/42 allows flow through the inner chamber 5 as indicated by the inhalation flow arrow. The positive pressure nozzle 20 is provided with gas under pressure from a positive pressure input port 18.

In FIGS. 1A and 1B, there is a pressurized gas input 30 that is connected to a source a pressurized gas (e.g. air, oxygen, etc.—not shown). A gas stream 9 flows out of a gas stream nozzle 41 and crosses the inner chamber 5 falling onto one of the receptor channels 32/36. As shown in FIG. 1A, when the patient is not inhaling (e.g., exhaling or at rest), the gas stream 9 flows directly across the inner channel 5 and into the first receptor channel 32. The first receptor channel 32 is fluidly interfaced to a first port 34 which is connected to an input 52 of a first pressure-to-movement conversion device 50 which is explained later.

As shown in FIG. 1B, when the patient is inhaling, the gas stream 9 flowing across the inner channel 5 is deflected and flows into the second receptor channel 36. The second receptor channel 36 is fluidly interfaced to a second port 38 which, in turn, is connected to an input 62 of a second pressure-to-movement conversion device 60 (see FIG. 2) which is explained later. In other embodiments, the gas stream (or jet) 9 is deflected or blocked by a device linked to a diaphragm, in particular for patients with very weak lung capacity.

Figure 4:
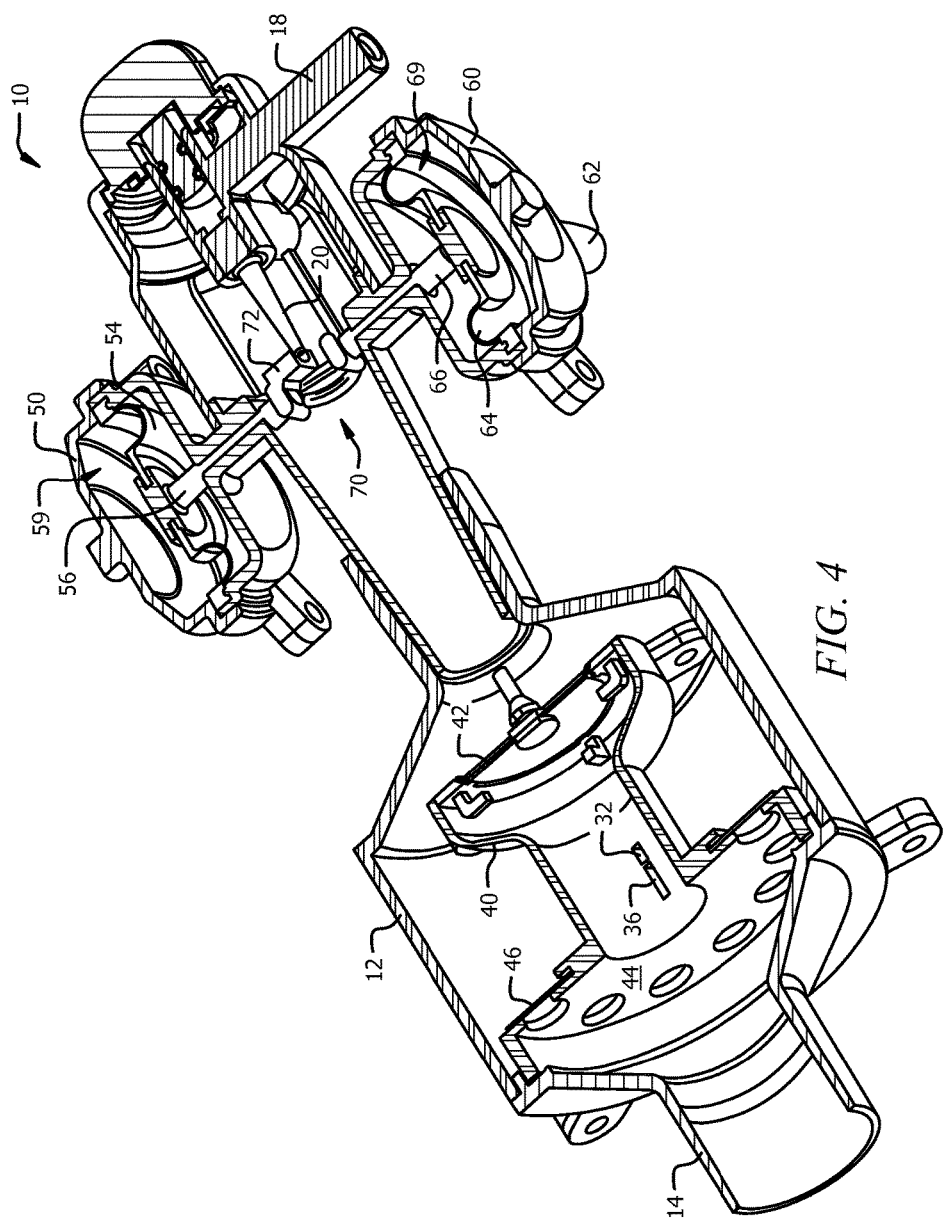
FIG. 4 illustrates another cut-away view of the mechanical bi-level positive airway pressure system.

The first pressure-to-movement conversion device 50 and the second pressure-to-movement conversion device 60 push and pull a movable occlusion device 70 that has an occluding member 72. The occluding member 72 is moved in front of the positive pressure nozzle 20 while the patient is not inhaling, thereby blocking gas pressure that continuously flows out of the positive pressure nozzle 20 until the patient starts to inhale. When the patient starts to inhale, the gas stream 9 flowing across the inner channel 5 is deflected and flows into the second receptor channel 36, which is in fluid communications with the second pressure-to-movement conversion device 60, which converts the gas pressure into a movement of the occluding member 72 to a position in which the gas pressure from the positive pressure nozzle 20 is no longer blocked, thereby providing positive pressure to the patient, helping the patient inhale. When the patient stops inhaling, the gas stream 9 flowing across the inner channel 5 relaxes and flows into the first receptor channel 32, which is in fluid communications with the first pressure-to-movement conversion device 50, which converts the gas pressure into a movement of the occluding member 72 to a position in which the gas pressure from the positive pressure nozzle 20 is blocked, thereby reducing the positive pressure and allowing for exhalation by the patient without needing to overcome the positive pressure. An example of pressure-to-movement conversion devices 50/60 and the occlusion system 70, including the occlusion device 72 is shown in FIG. 4. It is fully anticipated that in some embodiments, a single pressure-to-movement conversion device operates on a pressure from one or the other of the first receptor channel 32 or the second receptor channel 36 using a resilient member or the resiliency of the diaphragm to return the occlusion device to the correct position after abatement of the gas pressure. Therefore, it is fully anticipated that in some embodiments, a single pressure-to-movement conversion device 50/60 is used and resilient force is used to return the occlusion device 72 back to a resting position. For example, a single pressure-to-movement conversion device 60 fluidly interfaced to the second receptor channel, in which the single pressure-to-movement conversion device 60 has a resilient diaphragm in which the resilient diaphragm works to pull the occlusion device 72 into a resting position. When the patient inhales, the gas stream 9 flowing across the inner channel 5 bends and flows into the second receptor channel 36, thereby placing air pressure upon the resilient diaphragm, thereby overcoming the resilient force of the diaphragm and moving the occlusion device 72 away from the positive pressure nozzle 20, providing positive pressure to the patient. When the patient stops inhaling, the gas stream 9 flowing across the inner channel 5 retorts to its natural flow and no longer enters the second receptor channel 36 and the resilient force of the diaphragm moves the occlusion device 72 in front of the positive pressure nozzle 20, allowing the patient easier of exhalation.

A port 15 is provided to allow atmospheric air to flow in/out of the bi-level positive airway pressure system 10, allowing the exhalation gases to escape and allowing fresh air to enter during inhalation.

In some embodiments, the intermediate channel 16 between the positive pressure nozzle 20 and the detection section 12 is tapered to a narrower diameter to increase the velocity of the gas as it moves toward the patient. In some embodiments, the taper is a linear taper as shown in the figures.

Figure 2:
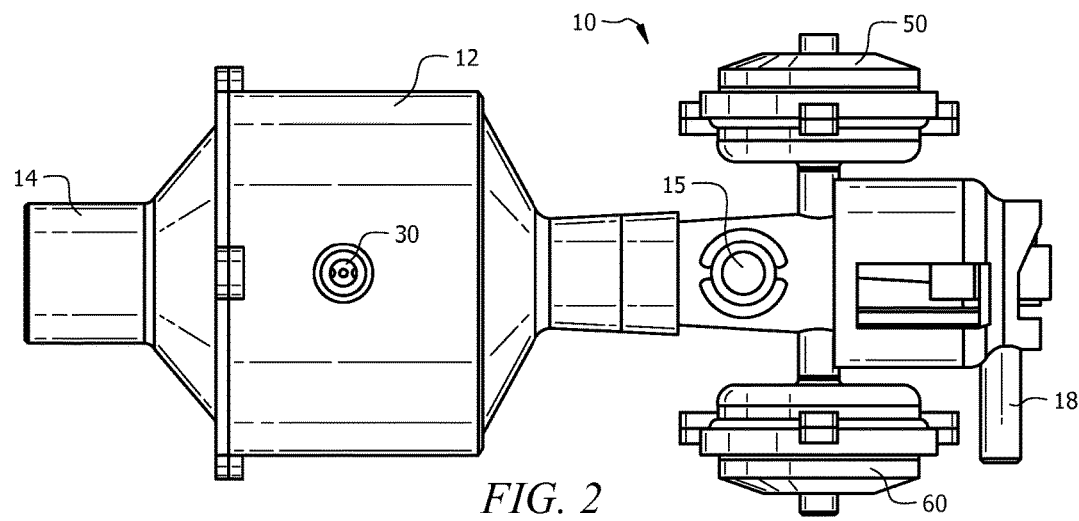
FIGS. 2 and 3 illustrate plan views of the mechanical bi-level positive airway pressure system.
Figure 3:
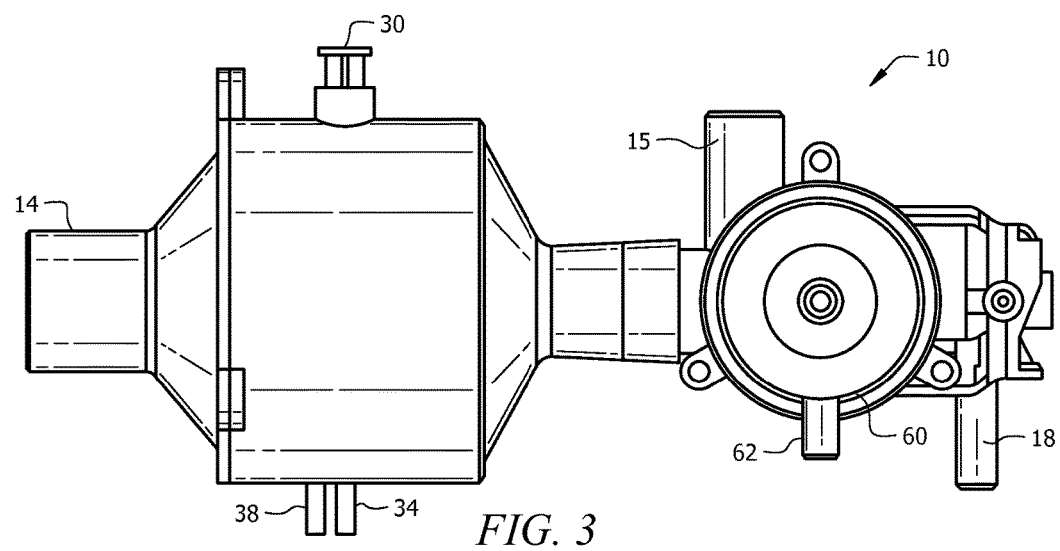

Referring to FIGS. 2 and 3, plan views of the mechanical bi-level positive airway pressure system 10 are shown. In this view, an exemplary outside enclosure 12 is visible as well as both pressure-to-movement conversion devices. Gas, under pressure, is connected to the pressurized gas input 30 to create the gas stream 9. Gas, under pressure, is also connected to the positive pressure input port 18. Although it is anticipated that the same source of pressurized gas is provided to both the pressurized gas input 30 and the positive pressure input port 18, it is also anticipated that in other embodiments, different sources of gas are used, in some embodiments being the same gas under different pressures and in some embodiments being different gases.

Referring to FIG. 4, another cut-away view of the mechanical bi-level positive airway pressure system 10 is shown. In this view, construction of exemplary pressure-to-movement conversion devices 50/60 and the occlusion system 70, including the occlusion device 72, is visible.

Each of the exemplary pressure-to-movement conversion devices 50/60 has a diaphragm 54/64 that is interfaced to a respective push rod 56/66. Air pressure from the respective ports 34/38 enter the pressure-to-movement conversion devices 50/60 from respective inputs 52/62 (see FIG. 5) that are in fluid communications with the outer chambers 59/69 surrounding the diaphragms 54/64. When air pressure enters the respective outer chamber 59/69, the air pressure pushes against the respective diaphragm 54/64, therefore, moving the respective push rods 56/66 in a direction towards the occlusion system 70. The push rods 56/66 are coupled to the occlusion system 70, thereby moving the occlusion device 72 either in front of the positive pressure nozzle 20 (during exhalation) or away from the positive pressure nozzle 20 (during inhalation).

Note that the exemplary pressure-to-movement conversion devices 50/60 are examples and many other devices are anticipated that perform similar functions in various ways, including using pistons, etc. Again, it is noted that it is anticipated that in some embodiments, only a single pressure-to-movement conversion device 50/60 is present.

Figure 5:
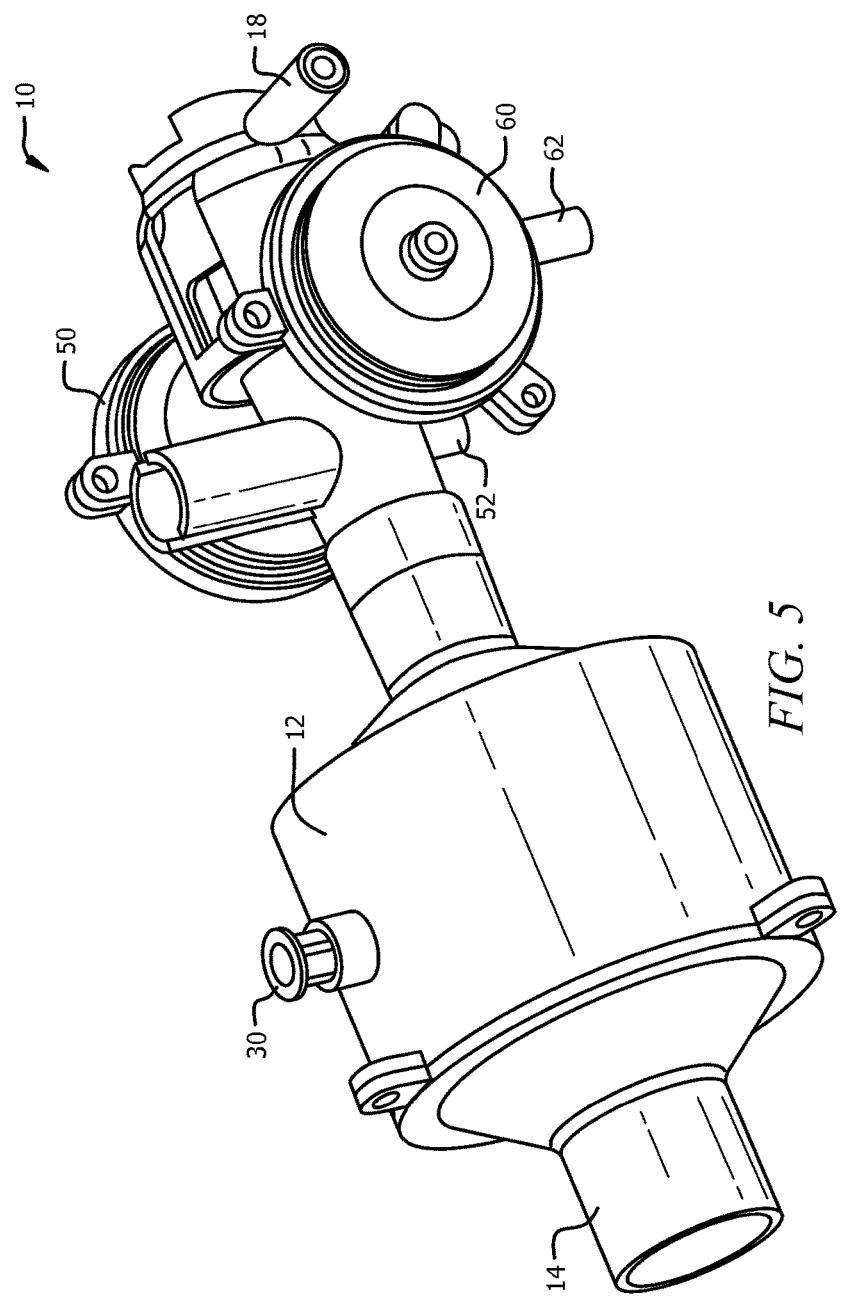
FIG. 5 illustrates a perspective view of the mechanical bi-level positive airway pressure system.

Referring to FIG. 5, a perspective view of the mechanical bi-level positive airway pressure system 10 is shown. It is anticipated that, for example, gas tubing connects both the pressurized gas input 30 and the positive pressure input port 18 to a source of pressurize gas (not shown for brevity reasons). It is also anticipated that the first port 34 is connected to the input 52 of a first pressure-to-movement conversion device 50 by a section of gas tubing (not shown for brevity reasons) and the second port 38 is connected to the input 62 of a second pressure-to-movement conversion device 60 by another section of gas tubing (not shown for brevity reasons). In alternate embodiments, it is equally anticipated that the first port 34 is directly connected to the input 52 of a first pressure-to-movement conversion device 50 through a channel formed in the body of the bi-level positive airway pressure system 10 and the second port 38 is directly connected to the input 62 of a second pressure-to-movement conversion device 60 through another channel formed in the body of the bi-level positive airway pressure system 10.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A bi-level positive airway pressure device comprising:
   a housing having a patient port for connecting to an airway of a patient;
   means for generating a positive airway pressure directed towards the patient port;
   mechanical means for detecting exhalation entering into the patient port;
   means for selectively blocking the means for generating positive airway pressure, the means for selectively blocking operative to block the positive airway pressure responsive to the means for detecting having detected exhalation;
   wherein the mechanical means for detecting comprises a gas jet directing a flow of a gas across an exhalation area such that in absence of exhalation, the gas jet is directed at a first port and in presence of the exhalation, the gas jet is deflected and directed at a second port.

2. The bi-level positive airway pressure device of claim 1, wherein the first port is interfaced to a first diaphragm and the second port is interfaced to a second diaphragm.

3. The bi-level positive airway pressure device of claim 2, wherein the first diaphragm upon receiving the gas jet moves the means for selectively blocking towards an unblocking position and the second diaphragm upon receiving the gas jet moves the means for selectively blocking towards a blocking position, thereby reducing positive air pressure while exhalation is detected by the mechanical means for detecting exhalation.

4. The bi-level positive airway pressure device of claim 1, wherein means for generating a positive airway pressure includes a nozzle, the nozzle directed towards the patient port, the nozzle connected to a source of gas pressure.

5. The bi-level positive airway pressure device of claim 4, wherein the housing has a taper between the nozzle and the patient port, the taper linearly decreases in diameter having the greatest diameter at a point closest to the nozzle.

6. The bi-level positive airway pressure device of claim 1, further comprising an exhalation one-way valve directing exhalation gases through an inner chamber of the housing and an inhalation one-way valve directing the positive airway pressure through an outer chamber of the housing, whereas the mechanical means for detecting is interfaced to the inner chamber.

7. The bi-level positive airway pressure device of claim 1, further comprising an exhalation one-way valve directing exhalation gases through an inner chamber of the housing and an inhalation one-way valve directing the positive airway pressure through an outer chamber of the housing, whereas the mechanical means for detecting is interfaced to the inner chamber and the gas jet is positioned on one side of the inner chamber and the first port and the second port are positioned on an opposite side of the inner chamber.

8. A bi-level positive airway pressure device comprising:
a housing having a patient port for connecting to an airway of a patient;
a nozzle for generating a positive airway pressure, the nozzle directed towards the patient port, the nozzle positioned near an end of the housing distal from the patient port;
mechanical means for detecting an exhalation flow entering into the patient port, the mechanical means for detecting coupled to a occluding member such that upon detection of the exhalation flow, the mechanical means for detecting causes the occluding member to block the nozzle, thereby abating the positive airway pressure;
wherein the mechanical means for detecting comprises a gas jet directing a flow of a gas across an exhalation area of the enclosure such that in absence of the exhalation flow, the gas jet is directed at a first port and in presence of the exhalation flow, the gas jet is deflected and directed at a second port.

9. The bi-level positive airway pressure device of claim 8, wherein the first port is interfaced to a first diaphragm and the second port is interfaced to a second diaphragm; the first diaphragm upon receiving the gas jet moves the occluding member towards an unblocking position and the second diaphragm upon receiving the gas jet moves the occluding member towards a blocking position, thereby reducing positive air pressure while exhalation flow is detected by the mechanical means for detecting exhalation.

10. The bi-level positive airway pressure device of claim 8, wherein the housing has a taper between the nozzle and the patient port, the taper linearly decreases in diameter having the greatest diameter at a point closest to the nozzle and a smallest diameter at a point closest to the patient port.

11. The bi-level positive airway pressure device of claim 8, further comprising an exhalation one-way valve directing exhalation flow through an inner chamber of the housing and an inhalation one-way valve directing the positive airway pressure through an outer chamber of the housing, whereas the mechanical means for detecting is interfaced to the inner chamber.

12. The bi-level positive airway pressure device of claim 8, further comprising an exhalation one-way valve directing exhalation gases through an inner chamber of the housing and an inhalation one-way valve directing the positive airway pressure through an outer chamber of the housing, whereas the mechanical means for detecting is interfaced to the inner chamber and the gas jet is positioned on one side of the inner chamber and the first port and the second port are positioned on an opposite side of the inner chamber.

13. A bi-level positive airway pressure device comprising:
a housing, a patient port at one end of the housing for interfacing to an airway of a patient;
a nozzle interfaced to a supply of gas, the nozzle generating a positive airway pressure in a direction aimed at the patient port, the nozzle situated at an end of the housing distal from the patient port and the nozzle is directed towards the patient port;
an occluding member movably positioned between the nozzle and the patient port, the occluding member positionable in at least two positions, a first position blocking the positive airway pressure and a second position allowing flow of the positive airway pressure to the patient port;
a gas jet initially aimed at a first port, the gas jet deflected by an exhalation flow to be aimed at a second port, the first port in fluid communications with a first mechanical device that moves the occluding member to the second position when the first mechanical device receives pressure from the gas jet, thereby enabling the positive airway pressure; and the second port in fluid communications with a second mechanical device that moves the occluding member to the first position when the second mechanical device receives pressure from the gas jet, thereby abating the positive airway pressure when the exhalation flow is detected.

14. The bi-level positive airway pressure device of claim 13, wherein the first mechanical device is a first diaphragm and the second mechanical device is a second diaphragm; the first diaphragm upon receiving the gas jet moves the occluding member towards an unblocking position and the second diaphragm upon receiving the gas jet moves the occluding member towards a blocking position, thereby reducing positive air pressure while exhalation flow is detected by the mechanical means for detecting exhalation.

15. The bi-level positive airway pressure device of claim 13, wherein the housing has a taper between the nozzle and the patient port, the taper linearly decreases in diameter having the greatest diameter at a point closest to the nozzle and a smallest diameter at a point closest to the patient port.

16. The bi-level positive airway pressure device of claim 13, further comprising an exhalation one-way valve directing exhalation flow through an inner chamber of the housing and an inhalation one-way valve directing the positive airway pressure through an outer chamber of the housing, whereas the gas jet, the first port, and the second port are interfaced to the inner chamber.

17. The bi-level positive airway pressure device of claim 16, wherein the gas jet is emitted from one side of the inner chamber and the first port and the second port are positioned on an opposite side of the inner chamber.

18. The bi-level positive airway pressure device of claim 17, wherein an area of the first port is smaller than an area of the second port.

* * * * *